United States Patent
Wood et al.

(10) Patent No.: US 7,498,450 B2
(45) Date of Patent: Mar. 3, 2009

(54) HOMOGENEOUS PROCESS FOR THE HYDROGENATION OF DICARBOXYLIC ACIDS AND/OR ANHYDRIDES THEREOF

(75) Inventors: Michael Anthony Wood, Yarm (GB); Simon Peter Crabtree, Durham (GB); Derek Vincent Tyers, North Yorkshire (GB)

(73) Assignee: Davy Process Technology Limited, London (GB)

( * ) Notice: Subject to any disclaimer, the term of this patent is extended or adjusted under 35 U.S.C. 154(b) by 0 days.

(21) Appl. No.: 10/577,340

(22) PCT Filed: Oct. 15, 2004

(86) PCT No.: PCT/GB2004/004397

§ 371 (c)(1), (2), (4) Date: Jan. 23, 2007

(87) PCT Pub. No.: WO2005/051875

PCT Pub. Date: Jun. 9, 2005

(65) Prior Publication Data

US 2007/0142679 A1    Jun. 21, 2007

(30) Foreign Application Priority Data

Oct. 31, 2003    (GB) ................... 0325526.2

(51) Int. Cl.
*C07D 407/00* (2006.01)
*C07D 305/00* (2006.01)
*C07C 407/00* (2006.01)

(52) U.S. Cl. .................. 549/328; 549/263; 549/295

(58) Field of Classification Search .................. None
See application file for complete search history.

(56) References Cited

U.S. PATENT DOCUMENTS

| | | | |
|---|---|---|---|
| 3,853,922 A | 12/1974 | Yamaguchi et al. | |
| 3,957,827 A | 5/1976 | Lyons | |
| 4,301,077 A * | 11/1981 | Pesa et al. | 549/508 |
| 4,377,715 A | 3/1983 | Nychka et al. | |
| 4,480,115 A | 10/1984 | McGinnis | |
| 4,485,245 A | 11/1984 | Hsu et al. | |
| 4,810,807 A | 3/1989 | Budge et al. | |
| 4,827,001 A | 5/1989 | Attig et al. | |
| 4,892,955 A | 1/1990 | Wada et al. | |
| 4,931,573 A | 6/1990 | Wada et al. | |
| 4,940,804 A | 7/1990 | Bohlendorf et al. | |
| 4,940,805 A | 7/1990 | Fischer et al. | |
| 4,965,378 A | 10/1990 | Budge et al. | |
| 4,973,713 A | 11/1990 | Manogue | |
| 5,021,589 A | 6/1991 | Wada et al. | |
| 5,037,996 A | 8/1991 | Suzuki et al. | |
| 5,047,561 A | 9/1991 | Miyazawa et al. | |
| 5,055,599 A | 10/1991 | Budge | |
| 5,072,009 A | 12/1991 | Budge et al. | |
| 5,077,442 A * | 12/1991 | Hara et al. | 568/864 |
| 5,079,372 A | 1/1992 | Wada et al. | |
| 5,099,038 A | 3/1992 | Suzuki et al. | |
| 5,196,602 A | 3/1993 | Budge et al. | |
| 5,426,246 A | 6/1995 | Nagahara et al. | |
| 5,473,086 A | 12/1995 | Budge et al. | |
| 5,478,952 A | 12/1995 | Schwartz | |
| 5,502,217 A | 3/1996 | Fuchikami et al. | |
| 5,580,991 A | 12/1996 | Sugiyama et al. | |
| 5,698,749 A | 12/1997 | Pedersen et al. | |
| 5,902,916 A | 5/1999 | Rühl et al. | |
| 5,936,126 A | 8/1999 | Rühl et al. | |
| 5,969,164 A | 10/1999 | Budge et al. | |
| 5,969,194 A | 10/1999 | Hara et al. | |
| 5,985,789 A | 11/1999 | Tooley et al. | |
| 6,008,384 A | 12/1999 | Bockrath et al. | |
| 6,077,964 A | 6/2000 | Tuck et al. | |
| 6,100,410 A | 8/2000 | Tuck et al. | |
| 6,204,395 B1 | 3/2001 | Tuck et al. | |
| 6,215,030 B1 | 4/2001 | Morikawa et al. | |
| 6,239,292 B1 | 5/2001 | Tuck et al. | |
| 6,274,743 B1 | 8/2001 | Tuck et al. | |

(Continued)

FOREIGN PATENT DOCUMENTS

CN    1286139 A    3/2001

(Continued)

OTHER PUBLICATIONS

Grey, Roger A., et al., "Anionic Metal Hydride Catlysts. 2. Application to the Hydrogenation of Ketones, Aldehydes, Carboxylic Acid Esters, and Nitriles", J. Am. Chem. Soc., 1981, p. 7536-7542, vol. 103, No. 25.

(Continued)

*Primary Examiner*—Karl J Puttlitz
(74) *Attorney, Agent, or Firm*—Senniger Powers LLP

(57) ABSTRACT

A homogeneous process for the hydrogenation of dicarboxylic acids and/or anhydrides in the presence of a catalyst comprising: (a) ruthenium, rhodium, iron, osmium or palladium; and (b) an organic phosphine; wherein the hydrogenation is carried out in the presence of at least about 1% by weight water and wherein the reaction is carried out at a pressure of from about 500 psig to about 2000 psig and a temperature of from about 200° C. to about 300° C. such that from about 1 mol to about 10 mol of hydrogen are used to strip 1 mole of product from the reactor.

20 Claims, No Drawings

U.S. PATENT DOCUMENTS

| | | |
|---|---|---|
| 6,288,245 B1 | 9/2001 | Bertola |
| 6,350,924 B1 | 2/2002 | Fischer et al. |
| 6,433,192 B1 | 8/2002 | Fischer et al. |
| 6,433,193 B1 | 8/2002 | Bertola et al. |
| 6,620,949 B1 | 9/2003 | Sutton et al. |
| 6,706,932 B1 | 3/2004 | Konishi et al. |
| 6,831,182 B2 | 12/2004 | Borchert et al. |
| 6,888,011 B2 | 5/2005 | Borchert et al. |
| 2004/0029728 A1 | 2/2004 | Borchert et al. |

FOREIGN PATENT DOCUMENTS

| | | |
|---|---|---|
| EP | 1077080 A1 | 2/2001 |
| JP | 02121976 A | 5/1990 |
| JP | 02200648 A | 8/1990 |
| JP | 02207081 A | 8/1990 |
| JP | 02233674 A | 9/1990 |
| JP | 02235880 A | 9/1990 |
| JP | 03074377 A | 3/1991 |
| JP | 03083974 A | 4/1991 |
| JP | 03112973 A | 5/1991 |
| JP | 04217636 A | 8/1992 |
| JP | 06107654 A | 4/1994 |
| JP | 06172338 A | 6/1994 |
| JP | 07033756 A | 2/1995 |
| JP | 07082260 A | 3/1995 |
| JP | 02200680 A | 1/2007 |
| WO | 9202298 A1 | 2/1992 |
| WO | 0134543 A1 | 5/2001 |
| WO | 0247815 A1 | 6/2002 |
| WO | 0247818 A1 | 6/2002 |
| WO | 0248129 A1 | 6/2002 |
| WO | 03093208 A1 | 11/2003 |

OTHER PUBLICATIONS

Hara, Yoshinori, et al., "Hydrogenation Reaction of Carboxylic Anhydrides Catalyzed by a New and Highly Active Cationic Ruthenium Complex", Chemical Letters, 1991, p. 553-554.

Inagaki, Hiroko, et al., "Hydrogenation Reaction of Carbonyl Compounds Catalyzed by Cationic Ruthenium Complexes", Science and Technology in Catalysis, 1994, p. 327-330.

International Search Report, PCT/GB2004/004397, dated Jan. 19, 2005, 2 pages.

Matteoli, Ugo, et al., "Homogeneous Catalytic Hydrogenation of the Esters of Bicarboxylic Acids Part III. Ethylene Glycol from Dimethyl Oxalate", Journal of Molecular Catalysis, 1988, p. 347-355, vol. 44.

Matteoli, Ugo, et al., "Structure and Catalytic Activity of Phosphine-Substituted Ruthenium Carbonyl Carboxylates", Journal of Organometallic Chemistry, 1995, p. 177-186, vol. 498.

Teunissen, Herman T., et al., "Homogeneous Ruthenium Catalyzed Hydrogenation of Esters to Alcohols", Chem. Commun., 1998, p. 1367-1368.

Teunissen, Herman T., et al., "Ruthenium Catalysed Hydrogenation of Dimethyl Oxalate to Ethylene Glycol", Chen. Commun., 1997, p. 667-668 and p. 1151.

* cited by examiner

HOMOGENEOUS PROCESS FOR THE HYDROGENATION OF DICARBOXYLIC ACIDS AND/OR ANHYDRIDES THEREOF

The present invention relates to a homogeneous process for the hydrogenation of dicarboxylic acids and/or anhydrides thereof. More particularly it relates to a continuous homogenous hydrogenation process which enables an efficient and cost effective means of recovering the product of the reaction. Most particularly it relates to a homogeneous process for the production of butanediol, tetrahydrofuran and/or γ-butyrolactone from maleic acid or maleic anhydrides.

Many catalyst systems are known which are suitable for use in the hydrogenation of carboxylic acids, acid anhydrides, esters or amides. Traditionally such reactions are carried out using heterogeneous catalysts and often high temperatures and pressures. A disadvantage of these heterogeneous catalyst systems is that many are intolerant of acid feedstocks and therefore have limited use.

For example, whilst copper based catalyst systems have been developed for use in the production of butanediol, tetrahydrofuran and/or γ-butyrolactone these are intolerant of acid and aqueous feedstocks and therefore the reaction must be carried out starting with maleic anhydride which must be esterified before reaction can be carried out. These additional process steps increase the processing costs and render the process less economical. To address this many suggestions have been made to integrate the maleic anhydride production with the hydrogenation of the maleic to the desired products.

To overcome this process heterogeneous precious metal systems have been developed that allow the use of an acid staring material in the presence of water. However, these require the use of exotic combinations of metals which have high cost implications both for production of the catalyst and recycling thereof.

Suggestions have been made relating to the use of supported ruthenium and ruthenium/tin catalysts for the production of butanediol, tetrahydrofuran and/or γ-butyrolactone. Whilst some of these are capable of reducing aqueous acid streams, the productivity of ethers is generally low and thus where the ether is the desired product a second reactor has to be included to convert the diols produced to the cyclic ethers which adds to the cost of the reaction. Examples of these catalyst systems can be found in U.S. Pat. No. 5,426,246, WO01/34543, U.S. Pat. Nos. 5,969,194, 5,985,789, 6,008,384, 5,478,952, WO92/02298, U.S. Pat. Nos. 4,973,713, 5,196,602, 4,827,001 and 4,301,077.

In order to overcome this problem, catalysts have been suggested for the hydrogenation of carboxylic acids and their derivatives based on ruthenium/phosphine systems. Examples of these catalyst systems include those described in U.S. Pat. Nos. 5,047,561, 5,079,372, 5,580,991, 5,077,442, 5,021,589, 4,931,573, 4,892,955, "Hydrogenation reaction of carboxylic anhydrides catalyzed by a new and highly active cationic ruthenium complex", Y-Hara et al Chem Lett (1991) 553, U.S. Pat. Nos. 3,957,827, 4,485,245 and 4,480,115 which are incorporated herein by reference.

However, whilst the systems described in these document provide processes which in general adequately enable hydrogenation reactions to be carried out, they do suffer from certain disadvantages and drawbacks. In particular, they require that the hydrogenation reaction is carried out in the absence of water since it is believed that any water present inhibits the catalyst or significantly reduces the rate of reaction. For example, in U.S. Pat. No. 5,047,561 an organic solvent is used and it is stated that the amount of water present should be controlled and should be no higher than 1% by weight. In "Hydrogenation reaction of carbonyl compounds catalyzed by cationic ruthenium complexes", H-Inagaki et al, Science and Technology of Catalysis (1994) 327 it is explained that the presence of water retards the hydrogenation reaction of succinic anhydride in the presence of a ruthenium trialkyl phosphine complexes in the presence of a promotor and that it is necessary to remove the water produced by hydrogenation in the gas stream and in U.S. Pat. Nos. 3,957,827 and 4,485,245 scavengers are used to remove any water produced in the reaction with the aim of improving yield and productivity.

Many of these known catalyst systems also require the presence of a promotor to increase the selectivity and activity of the ruthenium catalyst. Examples of such systems include those described in U.S. Pat. Nos. 5,079,372 and 4,931,573 where reactions are carried out in the presence of an organic solvent and a metal selected from Group IVA, VA and III is required as a promotor.

Another example of the use of a promotor may be found in U.S. Pat. No. 5,077,442. In this case a phosphorous compound is used to promote selectivity and conversion. This document teaches that any water produced in the reaction is removed from the reaction zone as the presence of water is said to decrease selectivity and conversion.

Another suitable promotor described is a conjugate base of an acid and in this connection reference may be made to U.S. Pat. Nos. 5,021,589 and 4,892,955. In this latter case, it is noted that components of the catalyst system are susceptible to hydrolysis under the reaction conditions and that a hydrogen purge was required to remove water produced during the reaction.

Whilst these processes go some way to providing adequate catalyst systems, there is still a need for an alternative process which allow for efficient hydrogenation of carboxylic acids and/or derivatives thereof with good conversion and selectivity to the desired products. As detailed in co-pending application no PCT/GB03/001819, which is incorporated herein by reference, it has been established that the presence of water is not only not disadvantageous but indeed offers positive advantages.

We have now established that a cost-effective process for the production of cyclic ethers, lactones and diols from dicarboxylic acids or anhydrides can be obtained in which the presence of the water allows for reaction conditions to be utilised in which the desired product can be continuously removed from the reactor using a much lower hydrogen stripping rate than has been achievable heretofore.

Thus, according to the present invention there is provided a homogeneous process for the hydrogenation of dicarboxylic acids and/or anhydrides in the presence of a catalyst comprising:

(a) ruthenium, rhodium, iron, osmium or palladium; and
(b) an organic phosphine;

wherein the hydrogenation is carried out in the presence of at least about 1% by weight water and wherein the reaction is carried out at a pressure of from about 500 psig to about 2000 psig and a temperature of from about 200° C. to about 300° C. such that from about 1 mol to about 10 mol of hydrogen are used to strip 1 mole of product from the reactor.

In particular the process of the present invention is a continuous process comprising the steps of:

(a) feeding the dicarboxylic acid and/or anhydride to the hydrogenation reactor;
(b) hydrogenating the dicarboxylic acid and/or anhydride;
(c) recovering the product in a hydrogen stream;
(d) separating the product from the hydrogen stream;

(e) recycling the hydrogen stream to the reactor;
(f) separating any removed catalyst and recycling the catalyst to the reactor; and
(g) recovering the product.

For the purposes of the present invention the term "dicarboxylic acid" includes both dicarboxylic acids and derivatives thereof such as mono- or di-esters. The dicarboxylic acid and/or anhydride may be saturated or unsaturated.

The dicarboxylic acid and/or anhydride is preferably a $C_4$ dicarboxylic acid or anhydride such that the process is a process for the production of butanediol, tetrahydrofuran and/or γ-butyrolactone. Where γ-butyrolactone is produced in the hydrogenation reaction it may be recovered or may be recycled to the hydrogenation reactor. The process may include a step for separating co-products.

Suitable $C_4$ starting materials include fumaric acid, maleic anhydride, maleic acid, succinic acid and succinic anhydride. These starting materials can be obtained from any suitable source. Maleic acid and anhydride can be produced by any suitable means for example by the oxidation of butane or benzene. Maleic anhydride is often recovered by partial condensation and/or in an absorber. If water is used in the absorber then some or all of the anhydride will be converted to the acid. The mixed water, acid and/or anhydride may be provided from the absorber to the reactor without the need for a separation step. If the acid is absorbed in a solvent, such as N-methylpyrrolidone then it can be fed directly into the reactor and the solvent recovered at the end of the reactor.

Where the starting feed is succinic acid it may be produced by the fermentation of aldose. Succinic acid may be fed to the reactor neat, in aqueous solution or in solution in a suitable solvent. Again, the solvent, such as N-methylpyrrolidone, can be fed directly into the reactor and the solvent recovered at the end of the reactor.

The feed may be pure or impure. For example, organic impurities such as those associated with the production of, for example, maleic acid and/or anhydride such as acetic acid, fumaric acid and/or acrylic acid may be present and will not effect the operation of the catalyst. Where acetic acid, fumaric acid and/or acrylic acid are present they may be reduced under the reaction conditions of the present invention. Thus, for example, acrylic acid may be reacted to form propionic acid, propanol and esters thereof.

By "homogeneous process" we mean that the catalyst is dissolved in the solvent for the reaction and that at least some of the water present and at least some of the dicarboxylic acid and/or anhydride must be in phase with the catalyst. Where excess water and/or dicarboxylic acid and/or anhydride is present, the excess may form a separate phase to that comprising the catalyst. Additionally or alternatively, the product may form a separate phase.

Where the dicarboxylic acid and/or anhydride is water soluble, the water may be present as the solvent for the reaction. Alternatively a solvent may be used. Where a solvent is used, the water will be present as an additive in the solvent or will be generated in-situ. In another alternative arrangement, the acid or its derivative or the product of the reaction may be the solvent.

Where the dicarboxylic acid and/or anhydride thereof is non-water soluble, such as for example for higher carbon content dicarboxylic acids and esters, the reactant or product may be the solvent for the reaction or an organic solvent may be used and the water may be present as an additive. In this case, it may be present in the solvent in an amount of from about 1% to the solubility limit of the water in the solvent. Additional water may be present in a separate aqueous phase.

In one alternative arrangement, the water may be produced in-situ as a by-product of the hydrogenation. Where the water is generated in-situ, if maximum benefits are to be achieved, the water should be generated within the first few cycles of the reaction. Where the water is to be generated in-situ, an amount of water may be added initially to cover the system's requirement until sufficient water has been generated.

It will therefore be understood, that the process of the present invention offers substantial advantages over the prior art arrangements in that water need not be removed from any reactants prior to the start of the reaction and may even be the solvent. Further, any water produced in the reaction need not be removed from the reactor. By this means, the known processes are simplified which will have cost implications. Further the use of the specified reaction conditions will enable the desired product to be removed from the reactor in a cost effective manner.

The reaction may take place in one or more reactors which are generally operated in series. The reactors may be stirred tank reactors. Where a plurality of reactors are used the product will typically be removed from the last reactor and the catalyst and hydrogen are preferably recycled back to the first reactor together with any unreacted starting material or intermediates.

The pressure of the reaction is from about 500 psig to about 2000 psig with pressures in the region of 900 psig being particularly preferred. The temperature of hydrogenation reaction is from about 200° C. to about 300° C. with temperatures in the region of about 240° C. to about 250° C. being particularly preferred.

As detailed above at these reaction conditions lower gas recycle rates may be used to remove the product of the reaction. For example, at a temperature of 240° C. and a pressure of 70 bara only 1.0 mols of gas are required to remove 1 mol of product tetrahydrofuran. This is in sharp contrast to a process carried out at 120° C. (such as would conventionally be used in the prior art) where 33.5 mols of gas are required to remove 1 mol of product. Since in commercial hydrogenation processes the capital and operating costs, particularly energy and other utility requirements, are largely determined by the flow rate of the gas. The size of the compressors, heat exchangers and interconnecting pipework is dictated by the gas flow rate and thus a reduction in the flow rate required to remove the product will enable a reduction in capital and operating costs.

At the operating conditions of the present invention a further advantage may be noted. Without wishing to be bound by any theory it is believed that in the reaction of maleic acid or anhydride to the formation of butanediol, tetrahydrofuran and/or γ-butyrolactone at the reaction conditions if desired any butanediol can be rapidly converted in-situ to tetrahydrofuran in the reactor. This may be required as tetrahydrofuran is a desirable end product and also because the removal of tetrahydrofuran may be found to be easier than that of the co-products. However, it will be understood that the relative distribution between butanediol, tetrahydrofuran and/or γ-butyrolactone can be altered by changing the phosphine used for the catalyst and controlling the concentration of free organic acids in the reactor.

A further advantage of the present invention is that with the low hydrogen stripping rate achieved in the present invention, in a process for the formation of butanediol, tetrahydrofuran and/or γ-butyrolactone, only water, tetrahydrofuran and low boiling impurities may be recovered. Butanediol, γ-butyrolactone, succinic acid etc will predominantly remain in the reactor where they will be converted to further tetrahydrofuran. Thus not only is the yield of the desired tetrahydrofuran increased but the costs implications of the need to separate co-products are avoided.

In one arrangement a cooler may be used on the exit gas from the reactor to further reduce the production of γ-butyrolactone.

Further, we have found that the presence of water is beneficial in terms of catalyst stability. It is noted that in prior art systems, decarbonylation of, for example, the product alcohols or intermediate aldehydes occurs and the carbon monoxide formed strongly inhibits the catalyst. To overcome this it is usual, in prior art arrangements, for the carbon monoxide to be removed and a methanation unit to be included in the plant to deal with recycling of vent gas to the reactor. However, this is unnecessary in the process of the present invention.

Without wishing to be bound by any theory it is believed that the presence of the water allows a side reaction to occur in the hydrogenation reactor in which any carbon monoxide produced reacts with the water to form carbon dioxide and hydrogen via the water gas shift reaction. This carbon dioxide and hydrogen may be further reacted to form methane. These gases can be readily removed from the reaction system thereby reducing the costs of the hydrogenation process. Thus, this system not only provides a cost-effective hydrogenation process but also obviates the need to have a separate methanation unit in the recycling system for vent gases.

A further advantage of the present invention is that the removal of the carbon monoxide as detailed above allows for effective regeneration of the catalyst. Thus the process offers extended catalyst life which in turn improves the economics of the reaction.

The water gas shift reaction does require heat for its initiation. Where the carboxylic acid and/or anhydride or the product of the hydrogenation is not thermally stable at the initiation temperature, the process of the present invention can be operated whereby the catalyst is allowed to be inhibited by the presence of generated carbon monoxide, the thermally unstable moiety is removed and the heat is then increased in the presence of the hydrogen such that the water gas shift reaction can operate to reactivate the catalyst for further reaction. By this means the process can be applied to a broad range of acids with prolonged catalyst life.

A still further advantage of the present invention is that there is no requirement to add buffer salts of the kind used in the prior art to stabilise the catalyst and further, promotors are not generally required and may, in some circumstances, even be deleterious. The reaction is preferably carried out in the absence of halides.

As described above, where the dicarboxylic acids and/or anhydrides are soluble in water, the water may act as the solvent. However, the method of the present invention may be conducted in the absence of a solvent, ie the starting material or reaction product may be a solvent for the reaction. However, if a solvent is used, any suitable solvent may be selected and examples of suitable solvents include, but are not limited to, diethyl ether, tetrahydrofuran, ethylene glycol dimethyl ether, dioxane, N-cyclohexylpyrrolidone, N-methylcaprolactam, 2-propanol, 2-butanol, secondary alcohols, tertiary alcohols, or toluene with tetrahydrofuran and other ethers being particularly preferred.

The preferred catalyst of the present invention is a ruthenium/phosphine catalyst. The ruthenium is generally provided as a ruthenium compound although halides are not preferred. Suitable compounds are those which can be converted to active species under the reaction conditions and include nitrates, sulphates, carboxylates, beta diketones, and carbonyls. Ruthenium oxide, carbonyl ruthenates and complex compounds of ruthenium, including hydridophosphineruthenium complexes, may also be used. Specific examples include, but are not limited to, ruthenium nitrate, ruthenium dioxide, ruthenium tetraoxide, ruthenium dihydroxide, ruthenium acetylacetonate, ruthenium acetate, ruthenium maleate, ruthenium succinate, tris-(acetylacetone) ruthenium, pentacarbonylruthenium, dipotassium tetracarbonyl-ruthenium, cyclo-pentadienyldicarbonyltriruthenium, tetrahydridedecacarbonyltetraruthenium, ruthenium dioxide, ruthenium tetraoxide, ruthenium dihydroxide, bis(tri-n-butylphosphine)tricarbonylruthenium, dodecacarbonyl-triruthenium, tetrahydridedecacarbonyltetraruthenium, undecacarbonyl-hydridetriruthenate. Where the catalyst is to be formed from rhodium, iron, osmium or palladium corresponding compounds may be used.

The ruthenium compound may be present in any suitable amount. However, it is preferably present in an amount of from 0.0001 to 5 mol, preferably 0.005 to 1 mol, as ruthenium per liter of reaction solution.

Any suitable phosphine may be used. Compounds which provide tridentate, bidentate and monodentate ligands may be used. Where the metal is ruthenium, tridentate phosphines are particularly preferred. Examples of suitable phosphine compounds include trialkylphosphines, dialkylphosphines, monoalkylphosphines, triarylphosphines, diarylphosphine, monoarylphosphines, diarylmonoalkyl phosphines and dialkylmonoaryl phosphines. Specific examples include but are not limited to tris-1,1,1-(diphenylphosphinomethyl) methane, tris-1,1,1-(diphenylphosphinomethyl)ethane, tris-1,1,1-(diphenylphosphinomethyl)propane, tris-1,1,1-(diphenylphosphino-methyl)butane, tris-1,1,1-(diphenylphosphinomethyl)2,2dimethylpropane, tris-1,3,5-(diphenylphosphinomethyl)cyclohexane, tris-1,1,1-(dicyclohexylphosphinomethyl)ethane, tris-1,1,1-(dimethylphosphinomethyl)ethane, tris-1,1,1-diethylphosphinomethyl)ethane, 1,5,9-triethyl-1,5-9-triphosphacyclododecane, 1,5,9-triphenyl-1,5-9-triphosphacyclododecane, bis(2-diphylephosphinoethyl) phenylphosphine, bis-1,2-(diphenyl phosphino)ethane, bis-1,3-(diphenyl phosphino)propane, bis-1,4-(diphenyl phosphino)butane, bis-1,2-(dimethyl phosphino)ethane, bis-1,3-(diethyl phosphino)propane, bis-1,4-(dicyclohexyl phosphino)butane, tricyclohexylphosphine, trioctyl phosphine, trimethyl phosphine, tripyridyl phosphine, triphenylphosphine with tris-1,1,1-(diphenylphosphinomethyl)-ethane being particularly preferred. Particularly advantageous results are achieved with tridentate facially capped phosphines with tris-1,1,1-(diarylphosphinomethyl)alkane and tris-1,1,1-(dialkylphosphinomethyl)alkane being particularly preferred.

The catalyst may be preformed or generated in-situ. Where an electron rich phosphine such as tris-1,1,1-(diethylphosphinomethyl)ethane is to be used it may be preferable to preform the complex in the absence of water prior to commencing the process of the present invention.

The phosphine compound may be present in any suitable amount. However, it is preferably present in an amount of from 0.0001 to 5 mol, preferably 0.005 to 1 mol, as phosphine per liter of reaction solution.

It will be understood that the process of the present invention is particularly suitable for use in a continuous system since the catalyst is not poisoned by carbon monoxide or if poisoning in this way occurs, the catalyst can be regenerated by reaction with the water.

Where the catalyst is removed from the reactor, for example, with a product removal stream, it may be recycled by any suitable means to the reactor.

The present invention will now be described with reference to the following examples which are not intended to be limiting on the scope of the invention.

EXAMPLE 1

Illustrates that maleic acid may be successfully hydrogenated in the presence of water.

Ruthenium(III)acetylacetonate (0.46 mmols, 0.181 g) and 1,1,1 tris(diphenylphosphinomethyl)ethane (triphos) (6.1 mmols, 3.8 g) and maleic acid (ex Fluka, 20.2 g) were transferred into a 300 ml Hastelloy Parr autoclave. This was sealed and purged with hydrogen before being pressurised to 700 psig with hydrogen and heated to 250° C. Once 250° C. had been achieved, the reactor was topped up with hydrogen to 1000 psig and this pressure was maintained throughout the reaction via a mass flow meter, which recorded the amount of hydrogen added. At the end of the reaction the hydrogen supply was isolated and the reactor cooled. At room temperature the headspace gas was analysed using a Pye-Unicam refinery gas analyser, before being vented. The product was removed from the reactor and weighed (91.42 g). The maleic conversion was determined by titration of the liquid product against 0.1 M sodium hydroxide (>99.9%). The water and organic analysis was determined using an HP gas chromatograph equipped with a micro TCD (wt %): water (86.52), propanol (0.84), tetrahydrofuran (7.02) propionic acid (0.14), γ-butyrolactone (2.47) butanediol (2.83); giving an overall molar selectivity to tetrahydrofuran of 51.1%, to γ-butyrolactone of 15.1%, and to butanediol of 16.5%.

COMPARATIVE EXAMPLE 1

Demonstrates that under the preferred reaction conditions the addition of sodium salts of strong acids is detrimental to the reaction reducing both the conversion and the selectivity. Example 1 was repeated except that two molar equivalents of sodium-p-toluene sulphonate were added. At the end of the reaction a white solid (succinic acid, 13.9 g) was recovered and the liquid products (82.5 g) were analysed by gas chromatograph and found to be (wt %) water (95.90) propanol (0.10), tetrahydrofuran (0.09), propionic acid (1.478) γ-butyrolactone (1.67), butanediol (0.38); giving an overall molar selectivity to tetrahydrofuran of 2.43% γ-butyrolactone of 38.25%, and to butanediol of 8.26%. Thus conversion had fallen to 33.49 mol %.

EXAMPLES 2

Illustrates the direct hydrogenation of succinic acid in the presence of a solvent In Example 2, Example 1 was repeated using except that maleic acid was replaces with succinic acid (20.03 g) 1-methyl-2-pyrrolidone (20.61 g) was included as a solvent and the 49.86 g water were used. At the end of the reaction the products were analysed and found to be (wt %) water (67.43), propanol (0.14) tetrahydrofuran (3.69), propionic acid (0.15) γ-butyrolactone (3.87), butanediol (5.22); giving an overall selectivity to tetrahydrofuran (32.55) γ-butyrolactone (42.91) and to butanediol of (9.57) and a conversion of >88%.

EXAMPLE 3

Illustrates the use of other tridentate facially co-ordinated phosphines.

Ru(acac)$_3$, (2.541 g) tris-1,1,1-(diethylphosphinomethyl) ethane (2.00 g) N-methylpyrrolidone (153 g) were loaded under argon into a 300 ml Hastelloy C autoclave, then heated at 200° C. for 30 minutes to preform the catalyst. The method of Example 1 was then repeated except that 15.89 N-methylpyrrolidone were added instead of the ruthenium acetylacetonate and triphos. At the end of the reaction the products were analysed and found to be (wt %) water (61.43), propanol (0.14) tetrahydrofuran (3.69), propionic acid (0.15), γ-butyrolactone (3.87), butanediol (5.22); giving an overall selectivity to tetrahydrofuran (30.49) to γ-butyrolactone (26.81) and to butanediol of (34.57) and a conversion of >99%

EXAMPLE 4

Illustrates that the catalysis may be performed on a continuous basis.

The continuous reactor consisted of an 800 ml Hastelloy Reactor equipped with a Parr Magana drive, gas induction stirrer, baffles and thermowell. Hydrogen (stripping gas) was supplied to the reactor via a Bronkhorst mass thermal flow controller. Nitrogen was regulated down to the desired pressure and supplied to the reactor, when required via a needle valve. 30 wt % maleic acid solution and deionised water were supplied to the reactor via two concept PUIII constametric pumps. During operation the maleic acid solution was added at a constant rate whilst the deionised water was added only to maintain the level in the reactor. The level in the reactor was monitored by the difference in temperature was then processed using a Moore's 351 controller to drive the deionised water constametric pump. Excess gas to that required in the reaction was added and the excess removed with the volatile products via a heated transfer line. The volatile products condensed in a condenser and were collected in a catch pot. The excess gas was vented through a backpressure regulator.

Ruthenium (III) acetyl$_a$cetonate (0.91 mmols 0.3606 g) and tris-1,1,1-(diphenylphosphinomethyl)ethane (1.1 mmols, 0.7081 g), 156.9 were transferred into the reactor. This was sealed, purged with nitrogen before being pressurised to 900 psig with nitrogen and this was set as the set point for the back pressure regulator, the stirrer started at 1000 rpm and the reactor was heated to 200° C. Once 200° was reached the reactor was left for 30 minutes. 150 g of 30 wt % maleic acid solution was pumped into the reactor and the water pump was turned on to maintain the level in the reactor and the hydrogen flow started at 100 NLPH. After a further hour the temperature of the reactor was increased to 250° C. Maleic acid solution was fed into the reactor at an initial rate of 0.5 mls/minute. After 228 hours on line a total of 7126 g of maleic acid and water had been fed and 6739 g of product recovered giving an overall mass balance of 95%. This was bulked and analysed, the water and organic analysis was determined using an HP gas chromatograph equipped with a micro TCD (wt %) water (89.17), propanol (0.17), tetrahydrofuran (4.33), propionic acid (0.52); γ-butyrolactone (5.79) others (0.02), giving an overall molar selectivity to tetrahydrofuran of 34%, and to γ-butyrolactone of 59%.

The invention claimed is:

1. A homogeneous process for the hydrogenation of dicarboxylic acids and/or anhydrides in the presence of a catalyst comprising:
   (a) ruthenium, rhodium, iron, osmium or palladium; and
   (b) an organic phosphine;
   wherein the hydrogenation is carried out in the presence of at least about 1% by weight water and wherein the reaction is carried out at a pressure of from about 500 psig to about 2000 psig and a temperature of from about 200° C.

to about 300° C. such that from about 1 mol to about 10 mol of hydrogen are used to strip 1 mole of product from the reactor.

2. A process according to claim 1 wherein the process is a continuous process comprising the steps of:
(a) feeding the dicarboxylic acid and/or anhydride to the hydrogenation reactor;
(b) hydrogenating the dicarboxylic acid and/or anhydride;
(c) recovering the product in an hydrogen stream;
(d) separating the product from the hydrogen stream;
(e) recycling the hydrogen stream to the reactor;
(f) separating any removed catalyst and recycling the catalyst to the reactor; and
(g) recovering the product.

3. A process according to claim 1 wherein the dicarboxylic acid and/or anhydride is a $C_4$ dicarboxylic acid or anhydride such that the process is a process for the production of butanediol, tetrahydrofuran and/or γ-butyrolactone.

4. A process according to claim 3 wherein any γ-butyrolactone produced in the hydrogenation reaction is recycled to the hydrogenation reactor.

5. A process according to claim 3 wherein the $C_4$ dicarboxylic acid or anhydride is fumaric acid, maleic anhydride, maleic acid, succinic acid or succinic anhydride.

6. A process according to claim 1 wherein the water is present as the solvent for the reaction.

7. A process according to claim 1 wherein one or both of the reactants or the product are the solvent for the catalyst.

8. A process according to claim 7 wherein a solvent is used and the water is present as an additive in the solvent.

9. A process according to claim 1 wherein the water is produced in situ as a by-product of the hydrogenation reaction.

10. A process according to claim 1 wherein the reaction takes place in more than one reactor and the reactors are operated in series.

11. A process according to claim 1 wherein the reaction is carried out at a pressure of about 900 psig.

12. A process according to claim 1 wherein the reaction is carried out at a temperature of about 240° C. to about 250° C.

13. A process according to claim 1 wherein the catalyst is a ruthenium/phosphine catalyst.

14. A process according to claim 1 wherein, the ruthenium is present in an amount of from 0.0001 to 5 mol as ruthenium per liter of reaction solution.

15. A process according to claim 1 wherein the phosphine is tridentate phosphine.

16. A process according to claim 1 wherein the phosphine is selected from trialkylphosphines, dialkylphosphines, monoalkylphosphines, triarylphosphines, diarylphosphine, monoarylphosphines, diarylmonoalkyl phosphines and dialkylmonoaryl phosphines.

17. A process according to claim 16 wherein the phosphine is selected from tris-1,1,1-(diphenylphosphinomethyl)methane, tris-1,1,1-(diphenylphosphinomethyl)-ethane, tris-1,1,1-(diphenylphosphinomethyl)propane, tris-1,1,1-(diphenylphosphinomethyl)butane, tris-1,1,1-(diphenylphosphinomethyl)2,2dimethylpropane, tris-1,3,5-(diphenylphosphinomethyl)cyclohexane, tris-1,1,1-(dicyclohexylphosphinomethyl)ethane, tris-1,1,1-(dimethylphosphinomethyl)ethane, tris-1,1,1 (diethylphosphinomethyl)ethane, 1,5,9-triethyl-1,5-9-triphosphacyclododecane, 1,5,9-triphenyl-1,5-9-triphosphacyclododecane, bis(2-diphylephosphinoethyl) phenylphosphine, bis-1,2-(diphenyl phosphino)ethane, bis-1,3-(diphenyl phosphino)propane, bis-1,4-(diphenyl phosphino)butane, bis-1,2-(dimethyl phosphino)ethane, bis-1,3-(diethyl phosphino)propane, bis-1,4-(dicyclohyxyl phosphino)butane, tricyclohexylphosphine, trioctyl phosphine, trimethyl phosphine, tripyridyl phosphine, and triphenylphosphine.

18. A process according to claim 16 wherein the phosphine is selected from tris-1,1,1-(diarylphosphinomethyl)alkane and tris-1,1,1-(dialkylphosphinomethyl)alkane.

19. A process according to claim 1 wherein, the phosphine is present in an amount of from 0.0001 to 5 mol as phosphine per liter of reaction solution.

20. A process according to claim 1 wherein the catalyst is regenerated in the presence of water and hydrogen.

* * * * *